United States Patent [19]

Wang

[11] Patent Number: 5,093,499

[45] Date of Patent: * Mar. 3, 1992

[54] SPIRODILACTAM DERIVATIVES

[75] Inventor: Pen-Chung Wang, Houston, Tex.

[73] Assignee: Shell Oil Company, Houston, Tex.

[ * ] Notice: The portion of the term of this patent subsequent to Jul. 3, 2007 has been disclaimed.

[21] Appl. No.: 506,394

[22] Filed: Apr. 9, 1990

[51] Int. Cl.$^5$ .................. C07D 487/10; C07D 493/10
[52] U.S. Cl. ..................................... 548/410; 549/265
[58] Field of Search ......................................... 548/410

[56] References Cited

U.S. PATENT DOCUMENTS 4,939,251 7/1990 Wang .................................. 548/410

Primary Examiner—Mark L. Berch

[57] ABSTRACT

Novel monomeric compounds containing aliphatic and-/or aromatic substituents on the 1,6-diazaspiro[4.4]nonane-2,7-dione ring system are produced by contacting an amine or an amine hydrohalide and a 1,6-dioxaspiro[4.4]nonane-2,7-dione or a 4-oxoheptanedioic acid. The resulting spirodilactam compounds are characterized by improved hydrolytic and thermal oxidative stability and some of the compounds are useful as intermediates to polymers containing the 1,6-diazaspiro[4.4-]nonane-2,7-dione ring system.

5 Claims, No Drawings

SPIRODILACTAM DERIVATIVES

BACKGROUND OF THE INVENTION

1. Field of the Invention

This invention relates to a novel class of spirodilactam derivatives. More particularly, the invention relates to 1,6-diazaspiro[4.4]nonane-2,7-dione compounds having aliphatic and/or aromatic substituents on the spiro ring nitrogen atoms.

2. Background of the Invention

In a series of copending U.S. patent applications of which allowed Ser. No. 245,618, filed Sept. 16, 1988, now U.S. Pat. No. 4,939,251, is illustrative, monomeric compounds containing the 1,6-diazaspiro[4.4]nonane-2,7-dione are disclosed and claimed. By way of specific illustration, compounds such as 1,6-di(4-hydroxyphenyl)-1,6-diazaspiro[4.4]nonane-2,7-dione are prepared. This compound is useful as a precursor of polymeric materials, both thermoplastic and thermoset, which would contain the 1,6-diazaspiro[4.4]nonane-2,7-dione ring system. Polymers containing the latter ring system have many useful properties. In some applications the polymers demonstrate thermal oxidative instability and sensitivity to water at elevated temperatures which can be detrimental if polymers containing these spirodilactam ring systems are exposed to moisture or oxygen at elevated conditions.

Without wishing to be bound by any particular theory, whatever instability is observed in the compounds is likely due to the presence within the molecule of active groups, including methylene hydrogen atoms which are alpha or adjacent to a carbonyl group. Any such difficulties of water or oxygen instability at elevated temperatures can be overcome by the substitution of the active methylene hydrogens with alkyl groups or other substituents. For example, there is disclosed in allowed Ser. No. 245,618, filed Sept. 16, 1988, the production of compounds containing a 3,3,8,8-tetramethyl-1,6-diazaspiro[4.4]nonane-2,7-dione ring system. Such ring substituted spirodilactams demonstrate greater thermal oxidative and hydrolytic stability at elevated temperatures.

It would be of advantage to provide new compounds having a spirodilactam ring system for various uses, including as intermediates to polymers or as compounds which are free of active methylene carbon atoms and therefore demonstrates greater stability towards oxygen and moisture at elevated temperature.

SUMMARY OF THE INVENTION

The present invention provides a class of 1,6-diaza[4.4]spirodilactam derivatives of improved stability. More particularly, the present invention provides a novel class of 1,6-diazaspiro[4.4]nonane-2,7-dione compounds.

DESCRIPTION OF THE INVENTION

The compounds of the present invention are 1,6-diazaspiro[4.4]nonane-2,7-dione compounds having saturated aliphatic and/or aromatic substituents of up to 18 carbon atoms, which are unsubstituted or inertly substituted by one or more of halogen, haloalkyl, nitro, nitroalkyl, alkyl, alkoxy, alkoxyalkyl, alkylthio, alkylthioalkyl, tertiary-amino or tertiary-aminoalkyl, on the spiro ring nitrogen atoms. Preferred members of this class have up to 60 carbon atoms. Compounds within the scope of the invention include those represented by the formula I

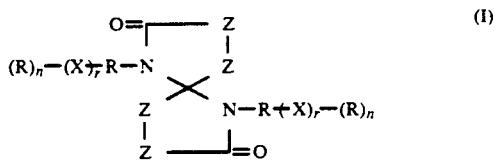

Z independently is >C(Z')$_2$ in which Z' independently is hydrogen, alkyl, particularly lower alkyl of up to 4 carbon atoms, inclusive, halo, particularly the lower halogens (fluoro or chloro), or aryl of up to 10 carbon atoms, particularly phenyl, or Z is such that two adjacent Z groups taken together form a ring system Z" of from 5 to 7 ring atoms, up to 2 of which are heteroatoms independently selected from nitrogen, oxygen or sulfur with the remainder of the ring atoms being carbon atoms, there being up to 15 carbon atoms in each Z", two of which ring carbon atoms form a bridge which connects a carboxy or carbonyl carbon with a spiro carbon atom common to the two indicated rings. The above term R independently is an aromatic, saturated aliphatic or aromatic and aliphatic group of up to 18 carbon atoms and is hydrocarbyl containing only atoms of carbon and hydrogen or is substituted hydrocarbyl containing additional atoms or groups, such as halogen or haloalkyl wherein the halogen is preferably middle halogen, chloro or bromo, or nitro, nitroalkyl, alkyl, alkoxy, alkoxyalkyl, alkylthio, alkylthioalkyl, tertiary-amino or tertiary-aminoalkyl in which the alkyl group is from 1 to 10 carbon atoms, preferably 1 to 4 carbon atoms in the form of monovalent substituents which are inert, at least under the conditions under which the spirodilactam compound is produced. Each R can contain up to 3 aromatic rings. The term X independently is a direct valence bond, alkylene of up to 8 carbon atoms inclusive, oxy, thio, sulfonyl, carbonyl, dioxyphenylene, 2,2-di(oxyphenyl)propane, di(oxyphenyl) sulfone or dioxydiphenylene, and each n and r independently is 0 or 1.

Compounds of the above formula I wherein the Z moieties are acyclic as not being part of a fused ring system, i.e., each Z is >C(Z')$_2$, are illustrated by 1,6-diphenyl-1,6-diazaspiro[4.4]nonane-2,7-dione, 3,8-dimethyl-1,6-diphenyl-1,6-diazaspiro[4.4]nonane-2,7-dione, 1,6-dibutyl-1,6-diazaspiro[4.4]-2,7-dione, 1,6-di(4-methoxyphenyl)-3,8-diphenyl-1,6-diazaspiro[4.4]nonane-2,7-dione, 1,6-di(4-phenylphenyl)-1,6-diazaspiro[4.4]-nonane-2,7-dione, 1,6-dioctyl-3,8-dichloro-1,6-diazaspiro[4.4]nonane--2,7-dione, 1,6-di(4-benzoylphenyl)-3,4,8,9-tetrafluoro-1,6-diazaspiro[4.4]nonane-2,7-dione and 1,6-dibenzyl-3,8-dibutyl-1,6-diazaspiro[4.4]nonane-2,7-dione.

The preferred spirodilactam compounds of the above formula are those wherein R is an aromatic or aromatic and aliphatic group. Examples of such aromatic groups for R include phenyl, biphenylyl, benzocyclobutane group, [2.2]-paracyclophanyl, acenaphthenyl, 1,2-acenaphthenylyl, bisphenylylmethyl, [2.2]-paracyclophanylmethyl, anthracenyl, naphthyl, benzyl, benzocyclobutenemethyl, and the like. Preferably each R independently is a phenyl group. Further preferred are such spirodilactams wherein each n and r is 0.

Within the spirodilactam ring system, the preferred spirodilactam compounds are those wherein each Z is $>C(Z')_2$ in which at least one $Z'$ on each $Z'$-substituted carbon atom is hydrogen or lower alkyl, particularly hydrogen.

The production of the spirodilactams of the invention comprises reaction between an amine or an amine salt, preferably an amine hydrohalide, and a spirodilactam precursor selected from a 1,6-dioxaspiro[4.4]-nonane-2,7-dione or a 4-oxoheptanedioic acid corresponding to the structure of the spirodilactam whose production is desired. In terms of the preferred spirodilactams of formula I, the amine or amine salt is a compound of up to 30 carbon atoms, inclusive, and is represented by the formula II $$(R)_r-(X)_n R-NH_2(\cdot HY)_m \qquad (II)$$

wherein R, X, n and r have the previously stated meanings; m is 0 or 1; and HY is an acid which forms a salt with the amine, including both inorganic and organic acids which do not interfere with the reaction, such as hydrohalogenic acids, such as hydrochloric and hydrobromic; sulfur acids, such as sulfuric or sulfonic; phosphorus acid, such as phosphoric or phosphonic; and organic acids, such as oxalic acid and the like. Preferably Y is halogen, e.g., fluorine, chlorine, bromine or iodine, but is more preferably middle halogen chlorine or bromine. In the process of the invention the presence of the amine, or at least a substantial proportion of the amine, can be used as the amine salt. Suitable amine (salts) of formula II include aniline (hydrochloride), 4-nitroaniline (sulfonate), 4-chloroaniline (hydrobromide), p-methoxyaniline (phosphate), 4-aminobiphenyl (hydroiodide), 4-aminodiphenyl sulfone (hydrochloride), 4-methylthioaniline (oxalate), 4-phenoxyaniline (hydrochloride), and 2,4-dimethylaniline (hydrochloride) and the like. Other amine (hydrohalide) precursors of the spirodilactams of the invention will be apparent from consideration of formula II and the components thereof.

The 4-oxoheptanedioic acid compound spirodilactam precursors are represented by the formula III $$\overset{A}{\underset{O=C}{|}}-Z-Z-\overset{O}{\underset{||}{C}}-Z-Z-\overset{A}{\underset{C=O}{|}} \qquad (III)$$

wherein Z has the previously stated meaning and A is hydroxy, lower alkoxy or halo, preferably middle halo.

When the Z moieties are linked together to form a ring system the ring system is aromatic, cycloaliphatic or heterocyclic and is hydrocarbyl containing only atoms of carbon and hydrogen besides any heteroatoms or substituted hydrocarbon containing additional atoms such as halogen, preferably middle halogen, in the form of inert carbon atom substituents.

In one embodiment employing the ketodiacid compound spirodilactam precursor, each Z moiety is $>C(Z')_2$ and the ketodiacid compound is an 4-oxoheptanedioic acid compound. In one such embodiment, largely because of a particularly convenient method of producing the spirodilactam precursor, a preferred 4-oxoheptanedioic acid compound has at least one hydrogen on the carbon atom adjacent to each carboxy function, that is, at least one $Z'$ on each carbon atom adjacent to a carboxy function is hydrogen. Such 4-oxoheptanedioic acid compounds are represented by the formula IIIa $$\overset{A}{\underset{O=C}{|}}-CHZ'-C(Z')_2-\overset{O}{\underset{||}{C}}-C(Z')_2-CHZ'-\overset{A}{\underset{C=O}{|}} \qquad (IIIa)$$

wherein $Z'$ and A have the previously stated meanings. Such 4-oxoheptanedioic acid compounds include 4-oxoheptanedioic acid, dimethyl 4-oxoheptane-dioate, 2,6dimethylheptanedioic acid, 2,3,5,6-tetramethyl-4-oxoheptanedioyl chloride, di-n-propyl 2,6-di-n-butyl-4-heptanedioate, 7-carbomethoxy-3,3,5,5-tetramethyl-4-oxoheptanedioic acid and the like. The preferred ketodiacids of the above formula IIIa are those wherein each $Z'$ is hydrogen or methyl, especially hydrogen, and each A is hydroxy or methoxy, especially hydroxy.

These ketodiacid compounds are known compounds or are produced by known methods, but the esters of formula IIIa, i.e., the compounds wherein A is alkoxy, are produced by reaction of formaldehyde with an $\alpha,\beta$-ethylenically unsaturated carboxylic acid ester such as methyl acrylate, ethyl methacrylate, methyl crotonate, methyl ethacrylate, propyl 2,3-dimethylbutanoate and the like. This reaction is conducted in the presence of a catalyst system which comprises a thiazolium salt and a tertiary amine and produces the dialkyl 4-oxoheptanedioate derivative in good yield. This process is described in greater detail in copending U.S. Pat. No. 4,800,231, incorporated herein by reference. Conversion of the esters thereby obtained to free acids or acid halides is by conventional methods as is the general interconversion of the acids, esters or acid halides of formula IIIa.

In a second embodiment of the ketodiacid compound spirodilactam precursor, the 4-ketodiacid incorporates cyclic moieties between the keto group and the carboxy functions, i.e., two adjacent Z moieties form a fused cyclic ring structure $Z''$. Such diacid compounds are represented by the formula IIIb $$\overset{A}{\underset{O=C}{|}}-Z''-\overset{O}{\underset{||}{C}}-Z''-\overset{A}{\underset{C=O}{|}} \qquad (IIIb)$$

wherein A and $Z''$ have the previously stated meanings. Illustrative of these cyclic ketodiacid compounds are di(2-carboxycyclohexyl) ketone, di(2-carboxyphenyl) ketone, di(2-carbopropoxycyclo-4-pentenyl) ketone, di(2-chlorocarbonylphenyl) ketone, di(2-carboxypyridyl) ketone, 2-carboxyphenyl N-methyl-3-carboxy-2-pyrryl ketone, di(3-carbethoxy-2-morpholinyl) ketone, di(3-carbomethoxy-2-napthyl) ketone and the like. The preferred cyclic ketodiacid compounds of formula IIIb are those wherein each $Z''$ is a ring system of from 5 to 6 carbon atoms inclusive and up to one nitrogen atom, particularly benzo.

Such ketodiacids are known compounds or are produced by known methods, such as the method of U.S. Pat. No. 1,999,181 or the method of Cava et al, J. Am. Chem. Soc., 20, 6022 (1955).

In yet another embodiment of the diketone compound spirodilactam precursor, the ketodiacid incorporates one fused cyclic moiety with the remainder of the Z moieties being $>C(Z')_2$, i.e., the compounds are of the formula IIIc

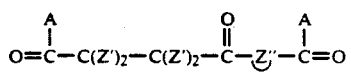

(IIIc)

wherein A, Z' and Z" have the previously stated meanings. Such ketodiacids of one cyclic moiety are illustrated by 3-(2-carboxybenzoyl)propionic acid, 3-(2-carbomethoxy-2-pyridyloyl)-2-ethylpropionic acid, ethyl 3-(2-carbethoxybenzoyl)propionate, 3-(2-carboxy-4-methylbenzoylbutyrl) chloride and the like. The ketodiacids of the above formula IIIc are known compounds or are produced by known methods. For example, 2-carboxymethylbenzaldehyde reacts with methyl acrylate according to the general teachings of U.S. Pat. No. 4,800,231, to produce methyl 3-(2-carbomethoxybenzoyl)propionate.

In a second modification of the invention, the spirodilactam precursor is a 1,6-dioxaspiro[4.4]nonane-2,7-dione compound wherein the spiro ring system is substituted with hydrogen, alkyl or halogen, or which incorporates fused cyclic substituents which include the 3- and 4- spiro ring positions and/or the 8- and 9- spiro ring positions of the spiro ring system.

The spirodilactone spirodilactam precursor, in terms of the spirodilactams of formula I, is represented by the formula IV

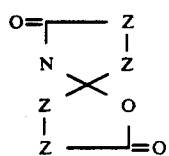

(IV)

wherein Z has the previously stated meaning.

In the embodiment of these spirodilactone spirodilactam precursors of the above formula IV wherein each Z is >C(Z')$_2$, the spirodilactone is represented by the formula IVa

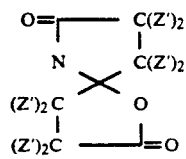

(IVa)

wherein Z' has the previously stated meaning. Illustrative of such spirodilactones are 1,6-dioxaspiro[4.4]nonane-2,7-dione, 3,8-dimethyl-1,6-dioxaspiro[4.4]nonane-2,7-dione, 3,4,8,9-tetramethyl-1,6-dioxaspiro[4.4]nonane-2,7-dione, 4,9-diphenyl-1,6-diazaspiro[4.4]nonane-2,7-dione, 3,3,8,8-tetramethyl-1,6-dioxaspiro[4.4]nonane-2,7-dione, 3,3,4,4,8,8,9,9-octamethyl-1,6-dioxaspiro[4.4]nonane-2,7-dione, 3,4,8,9-tetrafluoro-1,6-dioxaspiro[4.4]nonane-2,7-dione and the like. The preferred spirodilactones of the above formula IVa are those wherein at least one Z' of each Z'-substituted carbon atom is hydrogen.

The compounds of formula IVa are known compounds or are produced by known methods such as the process of Pariza et al, *Synthetic Communications*, Vol. 13(3), pp. 243-254 (1983), herein incorporated by reference.

In the embodiment of the spirodilactone spirodilactam precursors of the above formula IV which incorporate a fused cyclic moiety as a part of the two rings of the spiro ring system, the spirodilactones are represented by the formula IVb

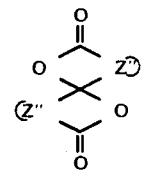

(IVb)

wherein Z" has the previously stated meaning. Typical compounds of this formula IVb are 3,4,8,9-dibenzo-1,6-dioxaspiro[4.4]nonane-2,7-dione, 3,4,8,9-di(cyclopentano)-1,6-dioxaspiro[4.4]nonane-2,7-dione, 3,4,8,9-di(4-methylbenzo)-1,6-dioxaspiro[4.4]nonane-2,7-dione, 3,4,8,9-di(pyrido)-1,6-dioxaspiro[4.4]nonane-2,7-dione and the like. These compounds are known compounds or are produced by known methods, for example, the process of the above Cava et al article or by the process of U.S. Pat. No. 1,999,181.

In a third embodiment of the spirodilactone spirodilactam precursor, a cyclic moiety is fused to one spiro ring and the other spiro ring is free from fused ring substituents. Such spirodilactones are represented by the formula IVc

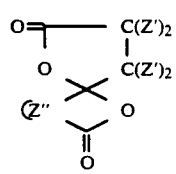

(IVc)

wherein Z' and Z" have the previously stated meanings. Such spirodilactones are illustrated by 3-methyl-8,9-benzo-1,6-dioxaspiro[4.4]nonane-2,7-dione, 3,4-benzo-1,6-dioxaspiro[4.4]nonane-2,7-dione, and 3,3,4,4-tetramethyl-8,9-morphoyl-1,6-diozaspiro[4.4]nonane-2,7-dione and the like. The spirodilactones of the above formula IVc are produced by known methods, for example, the dehydration of the corresponding ketodiacid. By way of illustration, 3,4-benzo-1,6-dioxaspiro[4.4]nonane-2,7-dione, is produced by dehydration of 3-(2-carboxybenzoyl)propionic acid through application of heat.

In general, the preferred spirodilactone spirodilactam precursors are hydrocarbon except for the oxygen atoms of the lactone moieties, and particularly preferred are those spirodilactones which are free from fused ring substituents (formula IVa) or those which have a fused ring substituent on each of the spiro rings (formula IVb). An especially preferred spirodilactone spirodilactam precursor of the first class is 1,6-dioxaspiro[4.4]nonane-2,7-dione.

The acyclic 4-oxoheptanedioic acid compounds are known or are produced by the methods described above, but certain of the esters are also produced by the reaction of formaldehyde and unsaturated carboxylic acid esters by the process disclosed and claimed in U.S. Pat. No. 4,800,231. Interconversion of the acids, esters or acid halides of formula III is by conventional methods. The production of 4-oxoheptanedioic acid compounds of formula III which contain cyclic moieties is by the process of Cava et al, *J. Am. Chem. Soc.*, 20, 6022 (1955). The spirodilactones of formula IVb are produced by the process of Pariza et al, *Synthetic Communications*, Vol. 13(3), pp. 243-254 (1983), or if the spirodilactones have additional fused rings by the process of U.S. Pat. No. 1,999,181.

The reaction of the amine or amine salt, e.g., hydrohalide, and the spirodilactone is conducted under reaction conditions in a liquid phase, preferably in the presence of a reaction diluent. When a diluent is present, the preferred reaction diluents are polar reaction diluents and are illustrated by ethers including acyclic ethers such as diethylene glycol dimethyl ether and tetraethylene glycol dimethyl ether as well as cyclic ethers such as tetrahydrofuran and dioxane, sulfur containing diluents such as sulfolane and dimethyl sulfoxide and N-alkylamides such as N,N-dimethylformamide, N,N-dimethylacetamide and N-methyl-2-pyrrolidone. In a preferred modification, however the polar reaction diluent is the amine corresponding to the amine salt (hydrochloride) reactant. The amine salt (hydrohalide), the spirodilactone and the reaction diluent are charged to a suitable reactor and maintained under reaction conditions. Suitable reaction conditions include an elevated reaction temperature of from about 25° C. to about 250° C., preferably from about 100° C. to about 200° C. In a particularly useful procedure, the reaction mixture is maintained at the reflux temperature of the mixture. Typical reaction pressures are up to about 10 atmospheres but more often from about 0.8 atmosphere to about 5 atmospheres. During reaction, the contact of the reactants is maintained by conventional procedures such as shaking, stirring or refluxing, and subsequent to reaction the desired 1,6-diaza [4.4] spirodilactam product is recovered from the product mixture by well known procedures such as distillation, diluent removal, precipitation or chromatographic methods.

The 1,6-diazaspiro[4.4]nonane-2,7-dione products of the invention are useful in a variety of applications, including those where the absence of activated methylene hydrogen atoms imparts hydrolytic and thermal oxidative stability. When the substituents on the spiro ring nitrogen atoms are substituted hydrocarbyl, advantage can be taken of the substituent groups to facilitate incorporation of the spirodilactam moieties into a polymeric chain. For example, 1,6-di(4-chlorophenyl)-1,6-diazaspiro[4.4]nonane-2,7-dione is reacted with an alkali metal salt of a bisphenol conventionally used in the art to produce a polyether which will have good properties at elevated temperatures because of the presence of the polycyclic structures in the polymeric chain. The 1,6-di(4-nitrophenyl)-1,6-diazaspiro[4.4]nonane-2,7-dione can be reduced using conventional methods known in the art, such as treating with hydrogen in the presence of platinum or heating with dilute hydrochloric acid in the presence of 10 to the corresponding 4-amino-substituted compounds, such as those disclosed and claimed in copending U.S. Ser. No. 314,513, filed Feb. 23, 1989, the disclosures of which are incorporated herein by reference. When the substituents of the spiro ring nitrogen atoms are hydrocarbyl, the compounds are useful as an ultraviolet (UV) stabilizer, plasticizer or flame retardants and the like.

The invention is further illustrated by the following Illustrative Embodiment which should not be regarded as limiting the invention in any way.

Illustrative Embodiment I

A mixture of 61.1 g (0.32 mole) of phenoxy aniline and 25 g of spirodilactone (0.16 mole) and 50 ml of m-cresol was placed in a 250 ml round-bottomed flask equipped with a mechanical stirrer and condenser and warmed with stirring to 165° C. After heating at 160°-170° C. for 24 hrs, the reaction mixture was cooled and poured into methanol to precipitate the model compound. The crude product was washed with methanol and dried in a vacuum oven at 120° C. overnight. The yield of the desired product was 80% and the m.p was 210°-212° C. The structure was confirmed by $C^{13}$ NMR to be consistent with that of 1,6-di(4-phenoxyphenyl)-1,6-diazaspiro[4.4]nonane-2,7-dione.

Illustrative Embodiment 2

A mixture of 9.3 g (0.1 mole) of aniline and 8.7 g (0.05 mole) of 4-ketopimelic acid and 20 ml of m-cresol was placed in a 250 ml round-bottomed flask equipped with a mechanical stirrer and condenser and warmed with stirring at 165° C. After heating at 160°-170° C. for 24 hrs. the reaction mixture was cooled and m-cresol was removed under reduced pressure. The product, an amber, thick liquid, was dried in a vacuum oven at 150° C. overnight. The structure of the desired product was confirmed by $C^{13}$ NMR to be consistent with that of 1,6-di(phenyl)-1,6-diazaspiro[4.4]nonane-2,7-dione. The yield was 80%.

What is claimed is:

1. The spirodilactam of up to 60 carbon atoms inclusive represented by the formula

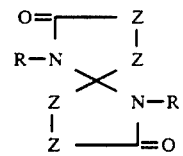

wherein Z independently is $>C(Z')_2$ in which Z' independently is hydrogen, lower alkyl, fluoro, chloro or aryl of up to 10 carbon atoms, and R independently is an unsubstituted or inertly substituted aromatic or saturated aliphatic group of up to 18 carbon atoms inclusive, wherein any such inert substituents independently are halogen, haloalkyl, nitro, nitroalkyl, alkyl, alkoxy, alkoxyalkyl, alkylthio or alkylthioalkyl in which each alkyl contains from 1 to 10 carbon atoms.

2. The spirodilactam of claim 1 wherein each Z is $>C(Z')_2$ wherein Z' is hydrogen or lower alkyl.

3. The spirodilactam of claim 2 wherein R is an unsubstituted or halo-substituted aromatic group.

4. The spirodilactam of claim 3 wherein at least one Z' of each $>C(Z')_2$ is hydrogen.

5. The spirodilactam of claim 4 of the structure 1,6-diphenyl-1,6-diazaspiro[4.4]nonane-2,7-dione.

* * * * *